(12) United States Patent
Jarrell

(10) Patent No.: US 7,911,609 B2
(45) Date of Patent: Mar. 22, 2011

(54) EVAPORATIVE LIGHT SCATTERING DETECTOR

(75) Inventor: Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 651 days.

(21) Appl. No.: 11/814,114

(22) PCT Filed: Jan. 11, 2006

(86) PCT No.: PCT/US2006/000903
§ 371 (c)(1),
(2), (4) Date: Jan. 25, 2008

(87) PCT Pub. No.: WO2006/083511
PCT Pub. Date: Aug. 10, 2006

(65) Prior Publication Data
US 2009/0027671 A1    Jan. 29, 2009

Related U.S. Application Data

(60) Provisional application No. 60/644,746, filed on Jan. 18, 2005, provisional application No. 60/672,939, filed on Apr. 19, 2005.

(51) Int. Cl.
*G01N 21/00* (2006.01)
(52) U.S. Cl. .................................................. 356/338
(58) Field of Classification Search ............ 356/334–342
See application file for complete search history.

(56) References Cited

U.S. PATENT DOCUMENTS

| | | | |
|---|---|---|---|
| 4,534,941 A | 8/1985 | Stephens et al. | |
| 4,958,529 A | 9/1990 | Vestal | |
| 5,247,842 A | 9/1993 | Kaufman et al. | |
| 5,433,189 A | 7/1995 | Bales et al. | |
| 6,229,605 B1 | 5/2001 | Benedict | |
| 6,362,880 B1 * | 3/2002 | Anderson et al. | 356/337 |
| 6,568,245 B2 | 5/2003 | Kaufman | |
| 7,268,881 B2 * | 9/2007 | Larsen et al. | 356/436 |
| 2003/0086092 A1 | 5/2003 | Gangloff et al. | |

FOREIGN PATENT DOCUMENTS

| | | |
|---|---|---|
| EP | 1275961 | 1/2003 |
| FR | 2827385 | 7/2001 |
| WO | 2004/077047 | 9/2004 |

OTHER PUBLICATIONS

Strode, III, J. Thompson B., et al; Evaporative Light Scattering Detection for Supercritcal Fluid Chromatography, vol. 34, Jun. 1996, pp. 261-271.
Demirbruker, M., et al; Miniaturized Light Scattering Detector for Packed Capillary Supercritcal Fluid Chromatography; J. Microcol. Sep. 5, 141-147 (1993).

(Continued)

*Primary Examiner* — Michael P Stafira
(74) *Attorney, Agent, or Firm* — Anthony J. Janiuk; William G. Guerin

(57) ABSTRACT

Embodiments of the present invention are directed to evaporation light scattering detectors having an evaporative chamber having a wall that is in good thermal contact with a heat sink. The heat has a high thermal mass such that a change in temperature of the wall during an analysis is minimized.

36 Claims, 13 Drawing Sheets

OTHER PUBLICATIONS

Figure 1:
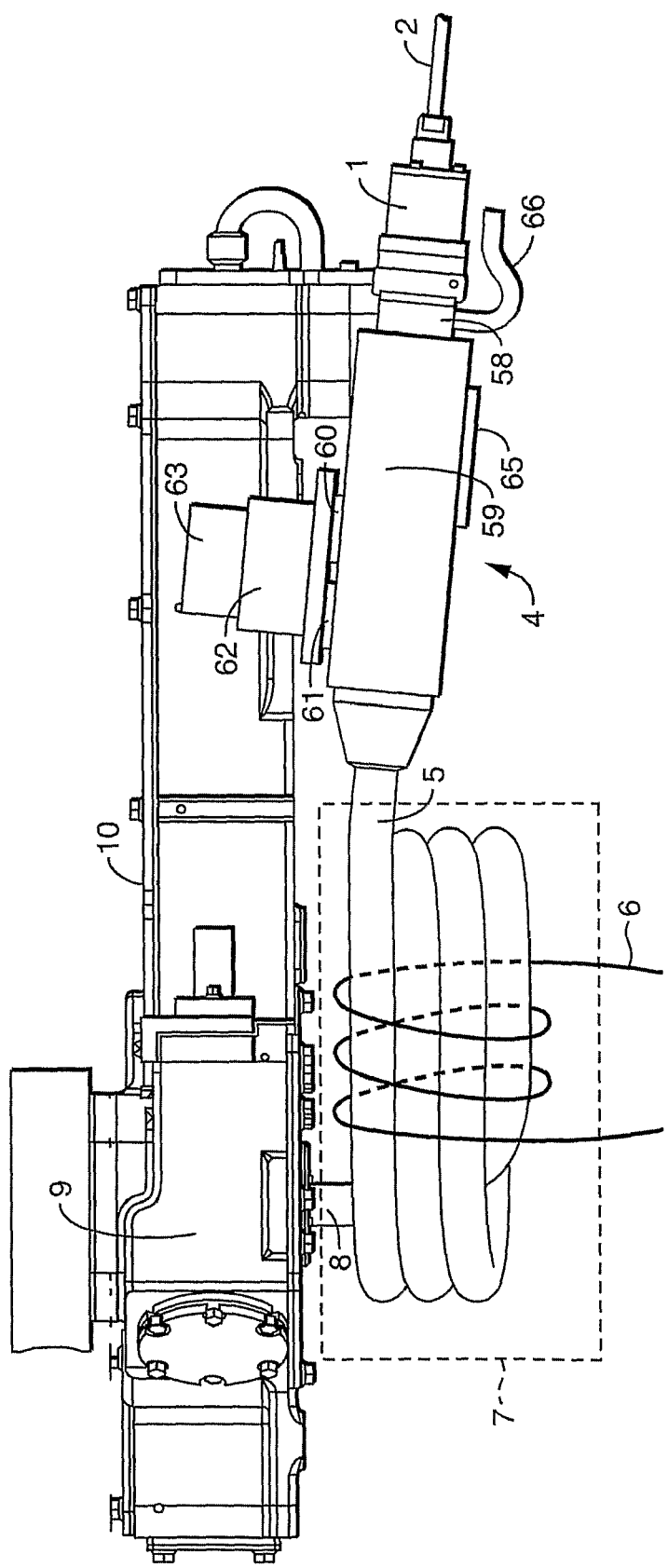

Nizery, D. et al; Improved Evaporative Light-Scattering Detection for Supercritical Fluid Chromatography With Carbon Dioxide-Methoanol Mobile Phases; Journal of Chromatography, 467 (1989) 49-60.

Berry, Anthony J. et al; Application of Packed-Column SFC Using Light-Scattering Detection; Journal of Chromatographic Science, vol. 34, May 1996, 245-253.

Brossard, S. et al; Comparison of ethoxylated alcohols and polyethylene glycols by high-performance liquid chromatography and supercritical fluid chromatography using evaporative light-scattering detection; Journal of Chromatography, 591 (1992) 149-157.

Stolyhwo, Andrezj et al; Use of Light Scattering As A Detector Principle In Liquid Chromatography, Journal of Chromatography. 265 (1983) 1-18.

Stolyhwo, Andrzej et al; Study Of The Qualitative And Quantitative Properties Of The Light-Scattering Detector, Journal Of Chromatography, 288 (1984) 253-275.

Deschamps, Frantz S. et al; Mechanism Of Response Enhancement In Evaporative Ligh Scattering Detection With The Addition Of Triethylamine And Formic Acid, The Royal Society Of Chemistry 2002, Analyst, 127, 35-41.

Demirbuker, M. et al; Miniatured Light Scattering Detector for Packed Capillary Supercritical Fluid Chromatography; J. Microcol. Sep. 5, 141-147 (1993).

Webster, Gregory K.; An Investigation Into Detector Limitations Using Evaporative Light-Scattering Detectors For Pharmaceutical Applications; Journal of Chromatographic Science, vol. 42, Oct. 2004.

Herbretau, Bernard, et al; Automatic Sugar Analysis In The Beet Industry; Part 1; Parameter Optimization Of A Reversed Phase HPLC Carbohydrate Determination; Journal of High Resolution Chromatography; vol. 13, Apr. 1990, 239-243.

Morin-Allory, Luc; Automatic Sugar Analysis In The Beet Industry; Part 2; Apparatus and Results; Journal Of High Resolution Chromatography; vol. 13, May 1990, 343-347.

Stockwell, P.B. et al; A Light Scattering Detector For Liquid Chromatography; American Laboratory, Aug. 1991, 19-21.

Nikolaos C. Megoulas et al, Twenty Years of Evaporative Light Scattering Detection, Critical Review in Analytical Chemistry, 2005, pp. 301-316, vol. 35, No. 4, CRC Press Inc.

Melissa J. Wilcox et al, A sensitive, flexible, dual-mode evaporative light scattering detector, American Laboratory, 1998, pp. 30-32, vol. 30, No. 17, International Scientific Communications, Inc.

Anonymous, SofTA Evaproative Light Scattering Detector, Jul. 19, 2004, XP002461689 Retrieved from the Internet: URL:http://web.archive.org/web/20040719150016/http://www.chromtech.com/online_catalog/instruments/detectors/ELSD.pdf.

* cited by examiner

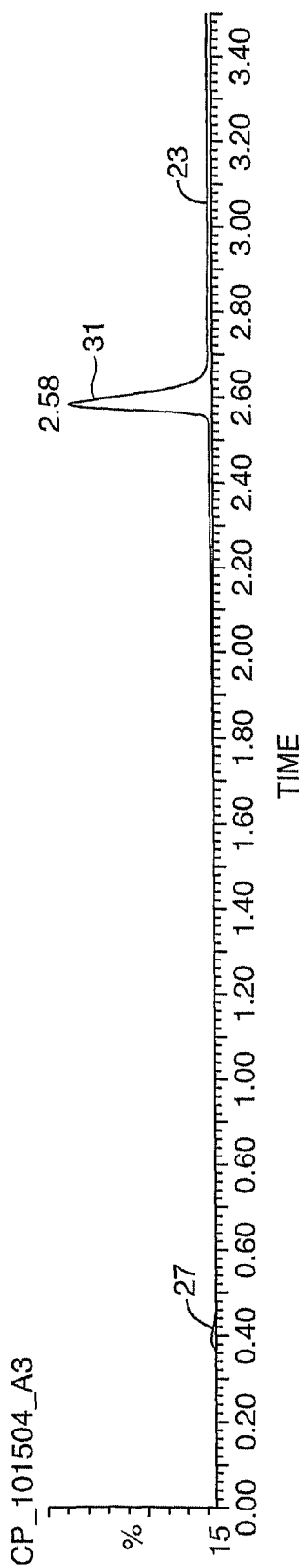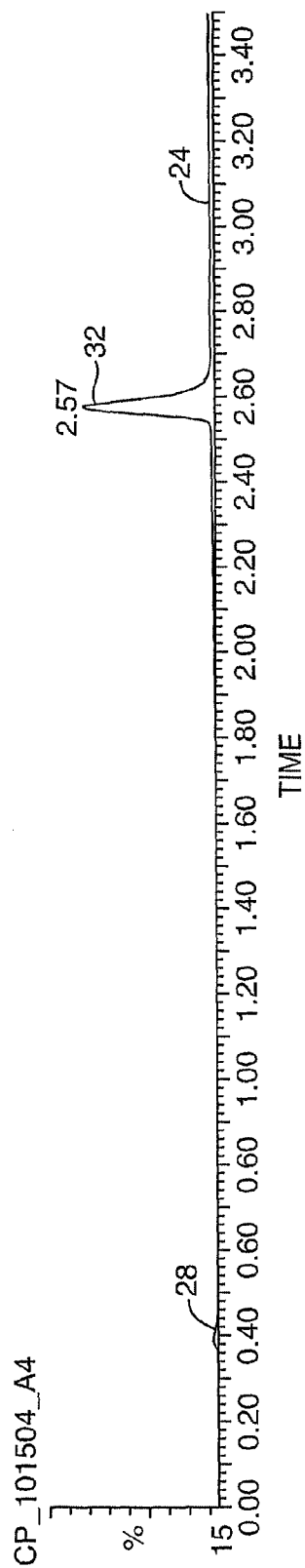

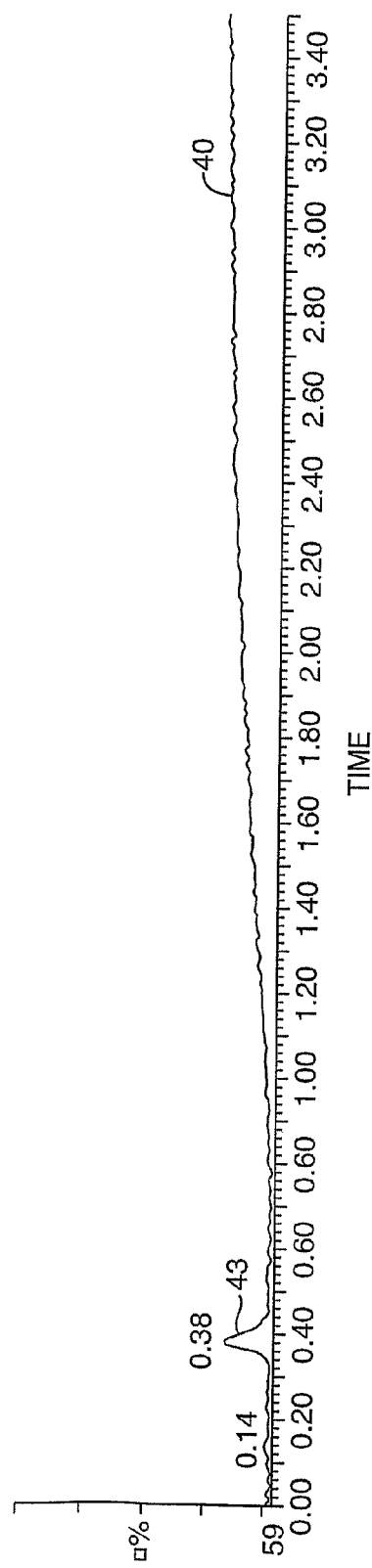

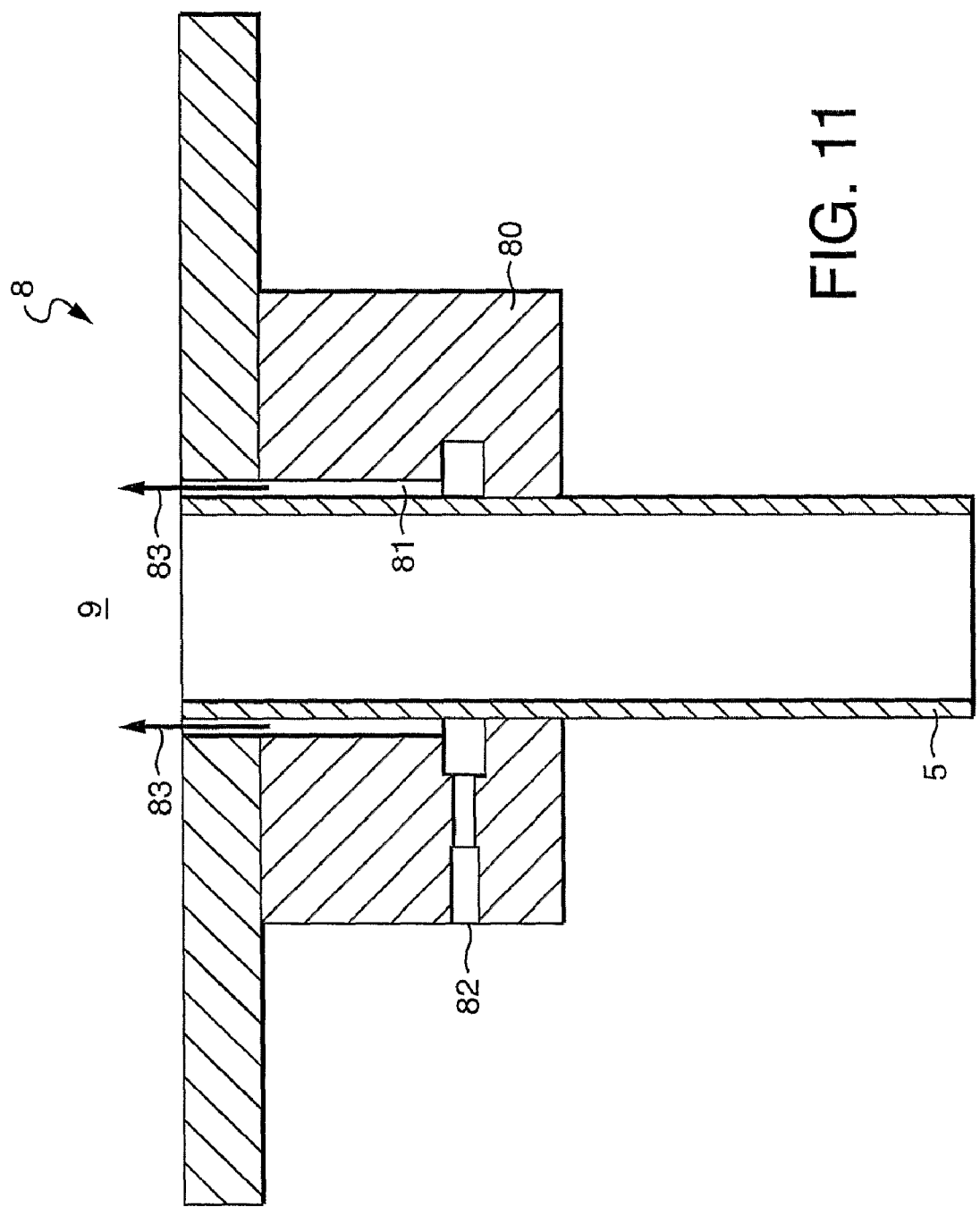

EVAPORATIVE LIGHT SCATTERING DETECTOR

CROSS REFERENCE TO RELATED APPLICATIONS

This application claims benefit of a U.S. Provisional Application No. 60/644,746, filed Jan. 18, 2005 and U.S. Provisional Application No. 60/672,939, filed Apr. 19, 2005. The contents of these applications are expressly incorporated herein by reference in its entirety.

FIELD OF THE INVENTION

This invention relates to improved evaporative light scattering detectors and methods of operating the same.

BACKGROUND OF THE INVENTION

Evaporative Light Scattering Detectors (ELSD) are commonly used in high performance liquid chromatography (HPLC) or supercritical fluid chromatography (SFC) because they are capable of detecting a wider variety of analytes than many other types of chromatographic detectors. Prior ELSD's comprise a nebulizer which receives the eluent from the chromatograph and generates an aerosol comprising droplets of the mobile phase. When an analyte elutes from the chromatograph these droplets will also comprise dissolved or suspended particles of the analyte. The aerosol generated by the nebulizer is passed into a heated desolvation region wherein the mobile phase evaporates leaving dry particles of the analyte. The particles then pass through a light beam and their presence is detected by measuring the scattered light from the beam.

The simplest prior ELSD's comprise a nebulizer, desolvation region and a light scattering region. An example of such a prior ELSD is given in U.S. Pat. No. 6,229,605 B1. Typically, the nebulizer is either a co-axial or cross-flow pneumatic nebulizer which uses a flow of inert gas to produce an aerosol from the eluent from the liquid chromatograph. This aerosol is generated directly in the desolvation region, which may comprise a heated drift tube, which solvent is evaporated from the aerosol. At the exit of the drift tube, desolvated analyte particles from the aerosol pass through a light beam, typically disposed perpendicularly to the direction of travel of the desolvated particles. Light scattered from the beam by the particles is detected by one or more detectors, (typically photomultipliers) disposed so that neither the particles themselves or the laser beam strike them. The signal from the detector(s) is amplified and fed to a display device such as a chart recorder or a computer for further processing.

The signal from the detector(s) is a measure of the quantity and size of analyte particles entering the laser beam, and hence a measure of the concentration of the analyte in the chromatograph eluent. As explained, an ELSD will produce a signal from almost all analytes providing that they are sufficiently involatile to avoid loss by evaporation in the drift tube. However, many factors affect the response of the ELSD, including the size and shape of the analyte particles, their chemical and physical properties, the nature and flow rate of the mobile phase, and the parameters of the nebulizer and drift tube, for example, nebulization gas flow and drift tube temperature. It is necessary to adjust these latter parameters carefully in order to obtain optimum performance, and the optimum values frequently depend on the mobile phase flow rate and composition, which can cause problems when gradient elution is employed.

It has been found that best results are obtained when the nebulizer generates an aerosol of relatively uniform droplet size. If it does not, large droplets may not be completely evaporated in the drift tube and may pass into the laser beam, generating signals even when no analyte is present in them. Increasing the drift tube temperature can help to evaporate those larger droplets, but risks evaporation of relatively volatile analytes because once the solvent is completely evaporated the temperature of an analyte particle may rise rapidly.

To mitigate the problem of droplet size, many ELSD's comprise a separate nebulizer chamber between the nebulizer itself and the heated drift tube.

The nebulizer chamber is typically unheated, so that the larger droplets in the aerosol separate out by condensation on the walls. A drain is provided to remove the condensed liquid. In some cases an impactor is provided, on which larger droplets in the aerosol will impinge and be lost, while smaller droplets are carried around it by the gas flow through the nebulizer chamber.

The average size of the droplets entering the heated drift tube is therefore smaller than it would be if the nebulizer chamber was not provided, which allows a lower drift tube temperature to be used while still completely desolvating the analyte particles. This in turn reduces analyte losses by evaporation. Use of a separate nebulizer chamber also facilitates operation with a supercritical fluid chromatograph, for example one using compressed carbon dioxide as a mobile phase.

A disadvantage of the additional chamber is, however, the loss of analyte that may be present in the larger droplets that condense in it, reducing sensitivity. Nevertheless, the majority of currently available ELSD's incorporate a separate nebulizer chamber. An example of such a commercially available ELSD is the Waters model 2420, (Waters Corporation, 34 Maple Street, Milford, Mass. 01757, USA). Other prior ELSD's comprising separate nebulizer chambers are described in WO 2004/077047, U.S. Pat. No. 6,362,880 and U.S. 2003/0086092 A1.

A typical application for an ELSD is for the HPLC analysis of complex mixtures of natural products. In these applications, the chromatographic separation may typically take between 20 and 120 minutes and large numbers of unknown compounds may be present. In such applications, the use of a UV-absorbance detector is risky because some of the unknown compounds may fail to be detected even when present in large concentrations, because they have no UV-chromophore. An ELSD has a more universal response and hence is more suitable in this application. Recently, ELSD's have begun to be used by chemists involved in the sythesis of new drug candidates by combinatorial chemistry. In this application, the HPLC analysis frequently last only 2 or 3 minutes. Unfortunately, prior ELSD's typically require as long as 15-20 minutes to stabilize at the commencement of an analysis, which increases the total analysis time by up to a factor of 10 and renders the use of the ELSD less cost effective in comparison with other detectors, despite its other advantages.

SUMMARY OF EMBODIMENTS OF THE INVENTION

It is an object of the present invention to provide ELSD's that are more stable in use than prior types. It is another object to provide ELSD's that have shorter stabilization times than prior types. It is a further object of the invention to provide a methods of operation of ELSD's which result in more stable operation and in a shorter stabilization time than prior methods.

In accordance with these objectives there is provided a detector for receiving the eluent from a liquid- or supercritical fluid-chromatograph in which a signal indicative of the presence of an analyte in said eluent is generated by the scattering of light by desolvated particles of said analyte, said detector comprising a nebulizer for generating an aerosol from said eluent in a chamber having a wall that is in good thermal contact with a first heat sink, said first heat sink having a high thermal mass such that the change in temperature of said wall during an analysis of said eluent is minimized.

Conveniently, the first heat sink may have a high thermal conductivity and may be comprised of a metal such as aluminium. The wall of the nebulizer and the first heat sink may comprise a single piece of high conductivity material, but preferably the wall is comprised of a chemically inert material such as stainless steel. In preferred embodiments the thermal mass of such a wall is kept to a minimum because its thermal conductivity is usually relatively low. The wall may be disposed in intimate thermal contact with the first heat sink to ensure that the temperature of the wall exposed to the aerosol is as close as possible to the temperature of the first heat sink.

In a particularly preferred embodiment, the nebulizer chamber may comprise an aluminium housing having a high thermal mass, the housing having a hollow cylindrical bore with a thin lining of stainless steel. In such an arrangement the aluminium housing may serve as the first heat sink and the lining of stainless steel may serve as the wall of the chamber.

In other embodiments the first heat sink may be fitted with a heat pump (for example, one or more Peltier effect devices) to transfer heat from it to a second heat sink. The second heat sink may be cooled by a fan. This arrangement may be used to cool the nebulizer chamber, prior to admission of eluent into the detector, to a sub-ambient temperature (for example, about 15° C.), as well as to help maintain the temperature of the chamber during an analysis.

In still other embodiments, a heater may be additionally or alternatively provided on the first heat sink. This may be used to help maintain the nebulizer chamber temperature when the nebulization of the eluent imposes a high cooling load, typically during the later stages of an analysis carried out at high eluent flow rates.

In another preferred embodiment, a temperature controller may be provided to maintain the temperature of the nebulizer chamber within specified limits. The temperature controller may control the power supply to any combination of the heat pump, fan and heater, where these are provided.

In yet another preferred embodiment, the invention comprises a nebulizer chamber as described above, a drift tube having an exit, said drift tube receiving and desolvating droplets of eluent from the nebulizer chamber, a light scattering chamber into which dry particles of analyte may pass from the drift tube, and a manifold surrounding said exit defining an annular space around said exit into which space a sheath gas may be introduced to confine said analyte particles within an annular flow of said sheath gas as they enter said light scattering chamber. The inventors have found that this reduces noise in the signal produced by the light scattered by the analyte particles.

The invention may also provide a method of detecting the presence of an analyte in the eluent from a liquid- or supercritical-fluid chromatograph in which the presence of an analyte in said eluent is indicated by the scattering of light by desolvated particles of said analyte, said method comprising nebulizing said eluent to produce an aerosol in a chamber having a wall, and minimizing the change in temperature of said wall during an analysis of said eluent by providing a first heat sink in good thermal contact with said wall, said first heat sink having a high thermal conductivity.

The invention may further provide a method of detecting the presence of an analyte in the eluent from a liquid- or supercritical-fluid chromatograph in which said presence is indicated by the scattering of light by desolvated particles of said analyte, said method comprising nebulizing said eluent to generate an aerosol in a chamber having a wall, and reducing the temperature of said wall at least prior to the analysis of said eluent and the generation of said aerosol.

Preferably, the temperature of the nebulizer chamber is reduced to a temperature below ambient temperature before the flow of eluent into the detector is started. Further, preferably the temperature may be reduced below 20° C. and most preferably to 15° C. or lower. The temperatures chosen may depend on the flow rate and composition of the eluent and may be chosen by experiment. Advantageously, a first heat sink may be provided in good thermal contact with the wall to stabilize the nebulizer chamber temperature, and further preferably the heat sink has a high thermal mass and a high thermal conductivity. Heat may be removed from the first heat sink to a second heat sink as previously described.

The inventors have found that providing a heat sink in contact with the wall of the nebulizer chamber stabilizes the temperature of the chamber and reduces the time taken for the detector to stabilize before an analysis can be commenced. Pre-cooling the heat sink as described may be carried out before the flow of eluent is started and may further reduce stabilization times and improve stability of the detector. The shortened stabilization times also reduce or eliminate the need to start the flow of eluent through the chromatograph and detector some time before an analysis is commenced, which is characteristic of prior detectors. This reduces waste of solvents.

BRIEF DESCRIPTION OF THE FIGURES

FIG. 1 is a drawing of a preferred embodiment according to the invention;

FIG. 2 is a schematic drawing of the main components of an optical bench suitable for use in a detector having features of the invention;

FIG. 3 is a sectional drawing of the nebulizer chamber of the detector shown in FIG. 1;

FIG. 4 is shows the variation of nebulizer chamber temperature with time during analyses carried out on two prior ELSD's and an ELSD as described herein;

FIG. 5 shows the variation of nebulizer chamber temperature at a later stage of the analyses of FIG. 4;

FIG. 6 shows the variation of nebulizer chamber temperature at a still later stage of the analyses of FIG. 4;

FIGS. 7A-7D show the chromatograms obtained using an ELSD as described herein for four consecutive injections of a sample;

FIGS. 8A-8E show the chromatograms obtained using an ELSD as described herein for different injection volumes of the same sample;

FIGS. 9A-9C show the chromatograms obtained using an ELSD as described herein for injections of different pure solvents;

FIG. 10 is a schematic drawing of a temperature control system suitable for use with a detector as described herein; and FIG. 11 is a sectional view of part of the apparatus of FIG. 1 suitable for use in certain preferred embodiments of a detector as described herein.

DETAILED DESCRIPTION OF EMBODIMENTS OF THE INVENTION

Figure 2:
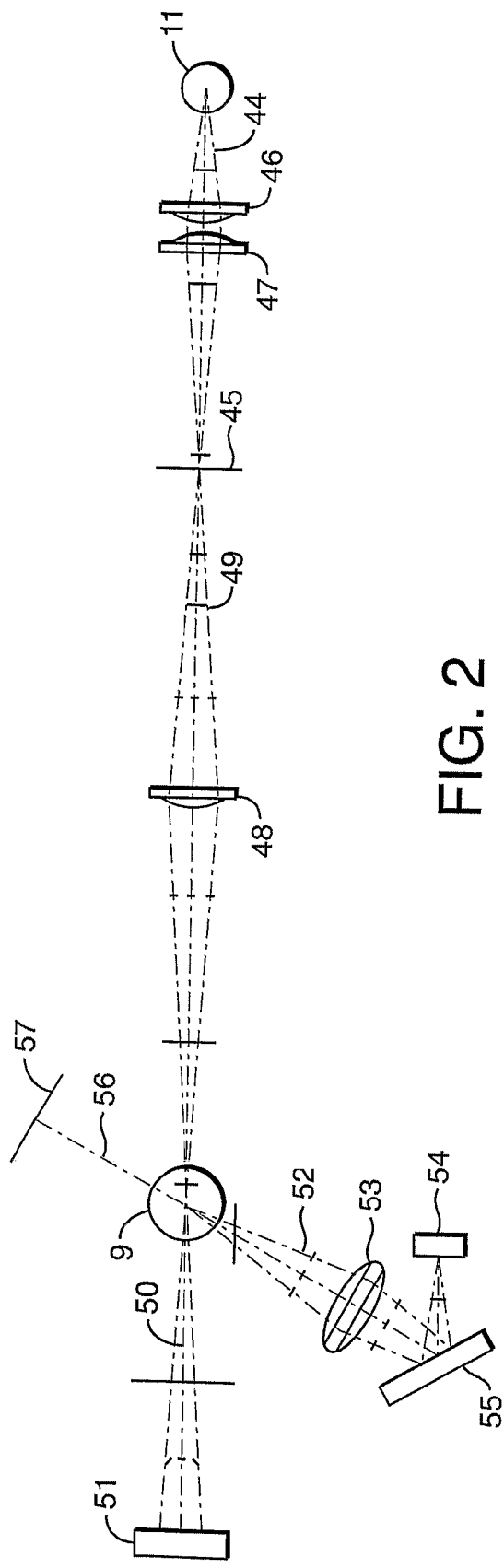

The principal components of a preferred embodiment of an ELSD according to the invention are shown in FIGS. 1 and 2. Eluent from a liquid- or supercritical-fluid chromatographic column enters a nebulizer 1 through an inlet pipe 2 and is nebulized to produce an aerosol 3 (FIG. 3) inside a nebulizer chamber 4. Nebulizer 1 is a coaxial-flow pneumatic nebulizer of the type used in prior ELSD's such as the Waters 2420 and need not be described in detail. Typically, a nebulizing gas flow rate of about 3 l/minute of nitrogen may be used for nebulizing a flow of 1 ml/minute of a mobile phase containing a high proportion of water.

Droplets of eluent produced by the nebulizer 1 are carried in the flow of nebulizing gas out of the nebulizer chamber 4 into a drift tube 5 that comprises a coil of thin-walled stainless steel tubing. Drift tube 5 is heated by an electrical heating tape (shown in part at 6) wrapped around it. An oven enclosure 7, packed with thermal insulation, encloses the drift tube 5 and heating tape 6. The temperature of the drift tube 5 is typically maintained at a temperature selected by the user in the range 30-50° C. A suitable temperature control system is described below. As in conventional prior ELSD's, droplets entering the drift tube 5 undergo desolvation so that any analyte present in them emerges as a stream of dry particles from an exit 8 of the drift tube 5 into an optical scattering chamber 9 comprised in an optical bench 10.

An optical bench 10 suitable for use in a detector according to the invention may comprise the bench used in the prior Waters 2420 ELSD. FIG. 2 is a schematic drawing illustrating the principle of operation of such a bench. A quartz/halogen lamp 11 produces a beam of light 44 that is focused on a slit 45 by two condensing lenses 46 and 47. The resulting beam is focused by a relay lens 48 to the centre of the scattering chamber 9, into which analyte particles to be detected are introduced from the exit 8 of the drift tube 5. The particles are introduced in a direction perpendicular to the plane of FIG. 2. A stray light baffle 49 is also provided. Unscattered light leaving the scattering chamber 9 is absorbed by a light trap 51, which also incorporates a photodiode (not shown). A signal from the photodiode may be used to monitor the intensity of the light entering the scattering chamber 9 and to ensure that the lamp 11 is serviceable.

Whenever an involatile analyte is present in the eluent entering the detector through inlet pipe 2, dry particles of analyte are swept from the drift tube 5 into the scattering chamber 9 and cause light to be scattered from the incoming light beam at a range of angles dependent on the nature and size of the particles. At least some of the light so scattered travels in a beam 52 and is focused by a lens 53 on to a photomultiplier 54 via an adjustable mirror 55. Light scattered in the opposite direction, that is along axis 56, is absorbed by a light trap 57.

The signal from the photomultiplier 54 may be amplified and digitized for further processing by a digital computer or microprocessor to yield a signal indicative of the quantity and size of analyte particles entering the scattering chamber 9. The electronic apparatus and software used for this purpose may be similar to that used in a conventional prior ELSD, such as the Waters 2420.

Figure 3:
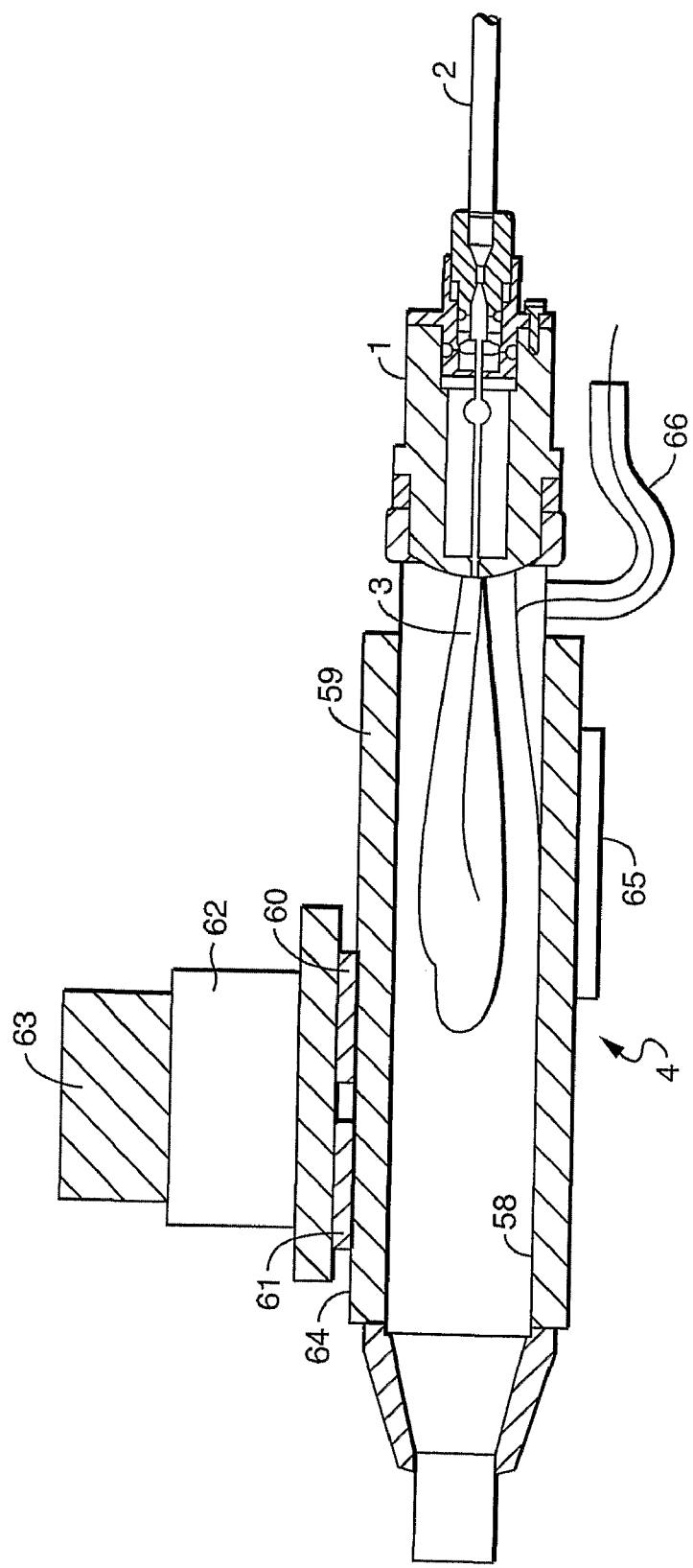

FIG. 3 is a sectional view of a nebulizer chamber 4 suitable for use in a detector according to the invention. It comprises a thin wall 58 of stainless steel formed into a cylindrical tube to define the chamber in which the aerosol 3 is formed. Wall 58 is in good thermal contact with a first heat sink 59 that comprises a rectangular-section block of aluminium having a high thermal mass surrounding the thin wall 58. Aluminium is a particularly suitable material for the first heat sink 59 because it has a high thermal conductivity, which ensures that temperature gradients along and around the wall 58 are minimized. The inventors have found that minimizing these gradients improves the performance of the detector. Other materials, for example, copper, brass, or other alloys that have high thermal conductivity, may also be used for the first heat sink 59. The wall 58 is preferably in good thermal contact with the first heat sink 59 over a substantial portion of its length. The inventors have found that minimizing the axial temperature gradient along the portion of the wall that is "visible" to the aerosol 3 also improves detector performance. Similarly, if the wall 58 is comprised of material having a relatively low thermal conductivity, for example stainless steel, it should have a relatively low thermal mass to ensure that the temperature distribution along its length is substantially determined by the first heat sink 58. Conveniently, the wall 58 may comprise a 3-inch long cylindrical tube of stainless steel having a wall thickness of 0.035 inches. The first heat sink 59 may comprise a 1.5 inch square section aluminium block bored out to receive the wall 58, as illustrated in FIG. 3. Heat sink 59 should extend as far as possible along the length of the wall 58, subject to the presence of other components associated with the nebulizer chamber 4, for example the nebulizer 1.

The wall 58 may also be comprised of glass, quartz, or ceramic, but it may be more difficult to ensure good thermal contact between these materials and the first heat sink 59, and the materials are typically more fragile.

It is also within the scope of the invention to manufacture the wall 58 and first heat sink 59 from the same material, for example, brass or ceramic having a high thermal conductivity, or even certain types of polymers or plastics. In this case, the two components may also comprise a single piece of material. The material should have as high a thermal conductivity as possible so that temperature gradients along it are minimized, and should have a high thermal mass, as discussed. These properties may conflict with the need to provide a chemically inert environment to surround the aerosol 3, but for many applications, an acceptable compromise may be found.

Two Peltier effect devices 60, 61 are attached to the first heat sink 59, A second heat sink 62, conveniently an aluminium block approximately 2 inches square, is attached to the other faces of the Peltier devices 60 and 61. A fan 63 is provided to cool the second heat sink 62. The Peltier effect devices comprise a heat pump 64 that removes heat from the first heat sink 59 and transfers it to the second heat sink 62. A heater 65 may also be fitted to the first heat sink 59.

In the complete detector assembly, the nebulizer chamber 4 may be orientated at a small angle relative to the horizontal, as shown in FIG. 1. This allows droplets of eluent that condense of the wall 58 to accumulate at the lowest point of the chamber. As in prior ELSD's such as the Waters 2420, a drain 66 configured as a siphon, is provided at this point, as shown in FIG. 1. This arrangement ensures that approximately the same level of condensed eluent is maintained in the chamber during operation, which improves stability. It may be necessary to fill the drain 66 with eluent prior to operation of the detector to ensure the best results.

Figure 10:
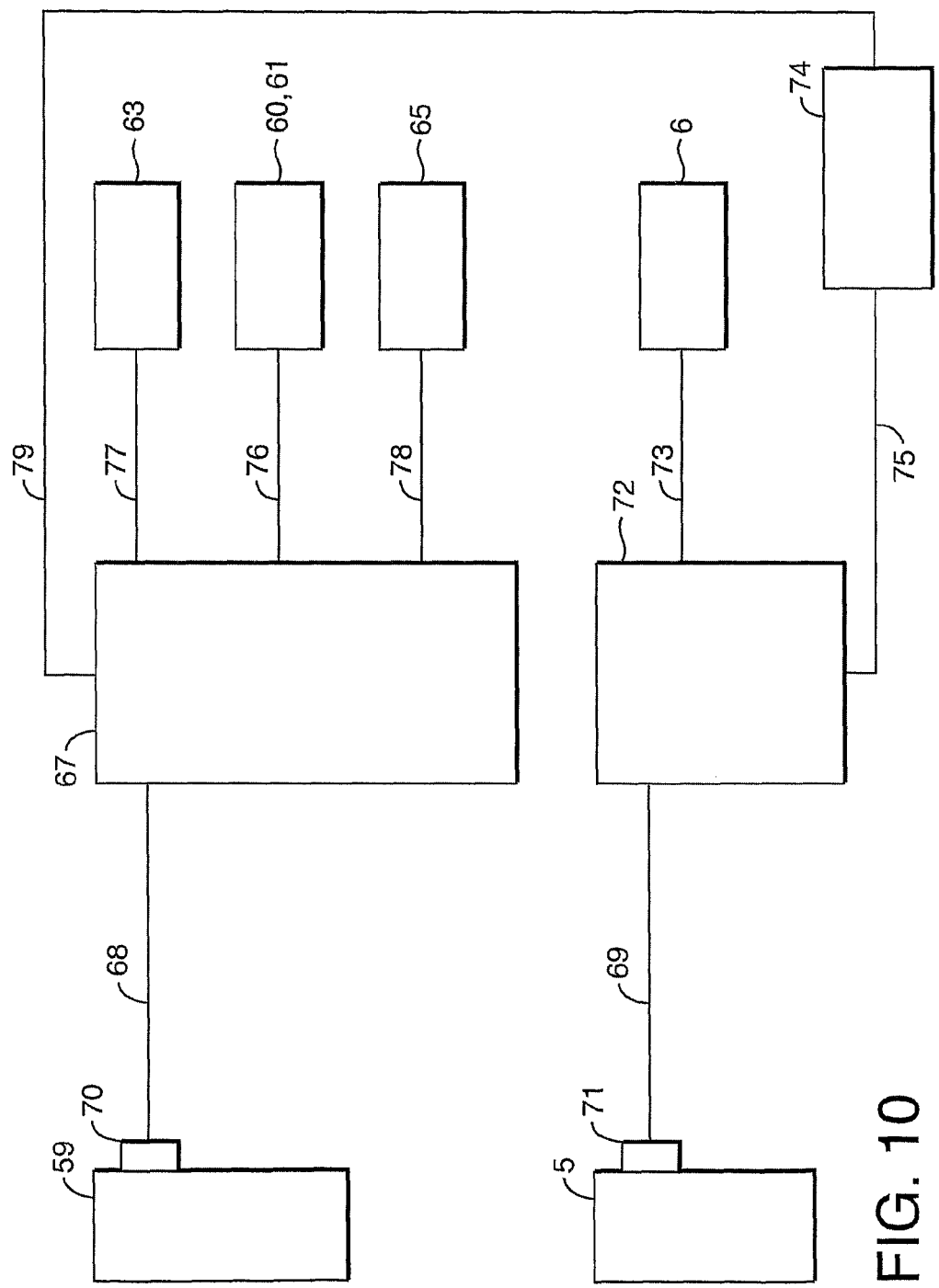

FIG. 10 is a schematic diagram of a temperature control system suitable for use in a detector as described. The system shown in FIG. 10 is not an essential feature of the invention, but may be used to further enhance performance. A first temperature controller 72 receives a signal via connection 69 from a temperature sensor 71 mounted on the drift tube 5. Controller 72 operates to maintain the temperature of the drift tube 5 at a predetermined value (chosen by the operator) by adjusting the power fed to the heating tape 6 via connection 73. A computer or microprocessor 74 may receive an input from a user specifying the chosen temperature, and may send a signal on connection 75 to controller 72 to set the desired temperature. Alternatively, an operator may set a chosen temperature directly on the controller 72. Typically, the drift tube temperature may be set in the range 30-50° C. according to the nature of the eluent and its flow rate. In the examples discussed below, a temperature of 48° C. was employed.

A second temperature controller 67 may receive a signal from a temperature sensor 70 mounted on the first heat sink 59 via connection 68. Controller 67 may control the power provided to the Peltier effect devices 60 and 61 via connection 76 to adjust the rate at which they transfer heat from the first heat sink 59 to the second heat sink 62. Additionally or alternatively, the speed of fan 63 may be controlled by controller 67 via connection 77 to vary the rate of cooling of the second heat sink 62 and thus control the temperature of the first heat sink 59. In another embodiment, an additional temperature sensor (not shown) may be provided on the second heat sink 62 to provide a signal to controller 67 which may then control the speed of fan 63 to maintain the temperature of the second heat sink 62 approximately constant.

The temperature controller 67 may also provide via connection 78 an output to a heater 65 mounted on the first heat sink 59. As explained, a preferred method of the invention involves the cooling of nebulizer chamber 4 below ambient temperature before the flow of eluent to the detector is started. Nebulization of the eluent tends to cause a further drop in temperature of chamber 4 (see examples discussed below) and in certain circumstances, it may be desirable to heat the chamber 4 rather than to cool it. If the signal from temperature sensor 70 indicates that the temperature of the first heat sink 59 is falling below the desired minimum, and the power supplied to the Peltier devices 60, 61 and/or the fan 63 is already low or zero, controller 67 may provide power to the heater 65 in place of the Peltier devices 60,61. It is within the scope of the invention for controller 67 to reverse the polarity of the power supplied to the Peltier devices 60 and 61 so that they transfer heat from the second heat sink 62 to the first heat sink 59 in order to increase its temperature. However, this mode of operation tends to reduce the lifetime of the Peltier devices and it is preferable to provide power to a separate heater and switch off the Peltier effect devices when additional heat input is required.

A computer 74 may receive an input from an operator that determines the desired temperature of the nebulizer chamber 4 and transmit this to controller 67 via connection 79.

In a preferred method of the invention, eluent from a liquid- or supercritical-fluid chromatographic column flows through the inlet pipe 2 into a nebulizer 1. A coaxial flow of nebulizing gas (for example, 3 l/minute of nitrogen) is introduced in a conventional way to generate an aerosol 3 (FIG. 3) inside a nebulization chamber 4. The temperature of the chamber 4 is maintained as described above. Droplets from the aerosol 3 may be passed into a heated drift tube 5 where the solvent is evaporated. Dry particles of any analyte present in the eluent may be swept from the drift tube 5 into a light scattering chamber 9 where they may scatter light from a beam 44 to be received by a photomultiplier 54, as described previously. In further preferred methods, the temperature of the nebulizer chamber 4 is stabilized by providing good thermal contact between its wall 58 and a first heat sink 59. Heat sink 59 has a high thermal conductivity and a thermal mass sufficient to minimize temperature fluctuations during a chromatographic analysis. In yet further preferred methods, heat may be pumped from the first heat sink 59 to a second heat sink 62 by a heat pump 64 which may comprise one or more Peltier effect devices 60, 61.

In another preferred method, the temperature of the nebulizer chamber 4 is reduced below ambient temperature before and analysis is commenced, and preferably before the flow of eluent into the detector is started. This may be achieved by operation of a heat pump 64 that may comprise one or more Peltier effect devices 60,61. Conveniently, the temperature may be reduced below 20° C., or most preferably to 15° C. or lower. Other preferred methods according to the invention may involve experimentally determining the most suitable operating temperature for the nebulizer chamber 4 before an analysis is commenced, for example by monitoring the change in temperature of the nebulizer chamber 4 when a gradient elution similar to that to be used for an analysis is run into the detector in the absence of an analyte.

Yet further preferred methods may comprise controlling the temperature of nebulizer chamber 4 by means of a temperature controller 67. The method may involve controlling the power provided to Peltier effect devices 60,61, a fan 63 on the second heat sink 62, and/or a heater 65 on the first heat sink 59, in order to maintain the temperature of the nebulizer chamber 4 approximately constant.

Referring next to FIG. 11, in a yet further preferred embodiment of the invention the exit 8 of the drift tube 5 is surrounded by a manifold 80 which defines an annular space 81 around the end of the tube where it enters the light scattering chamber 9. A sheath gas (conveniently nitrogen or dry air) is introduced through an inlet 82 in the manifold 80 so that it flows through the annular space 81 around the drift tube and into the light scattering chamber 9, as indicated by the arrows 83. Analyte particles exiting from the drift tube are in this way confined within an annular flow of gas as they enter the scattering chamber. The inventors have found that this stabilizes the flow of particles into the scattering chamber 9 and reduces noise in the signal from the photomultiplier 54 which results from the light scattered by the particles.

Working Examples

Figure 4:
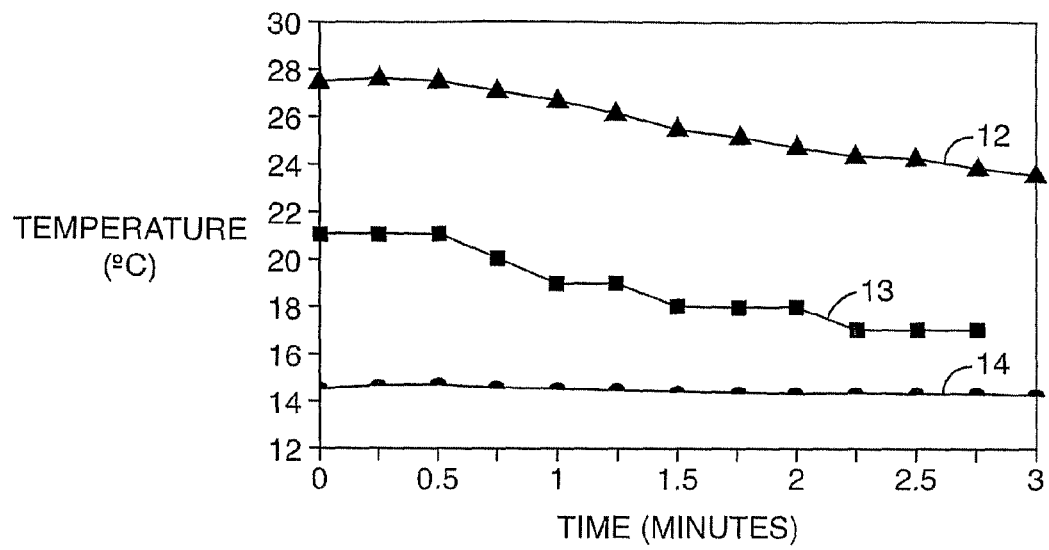
Figure 5:
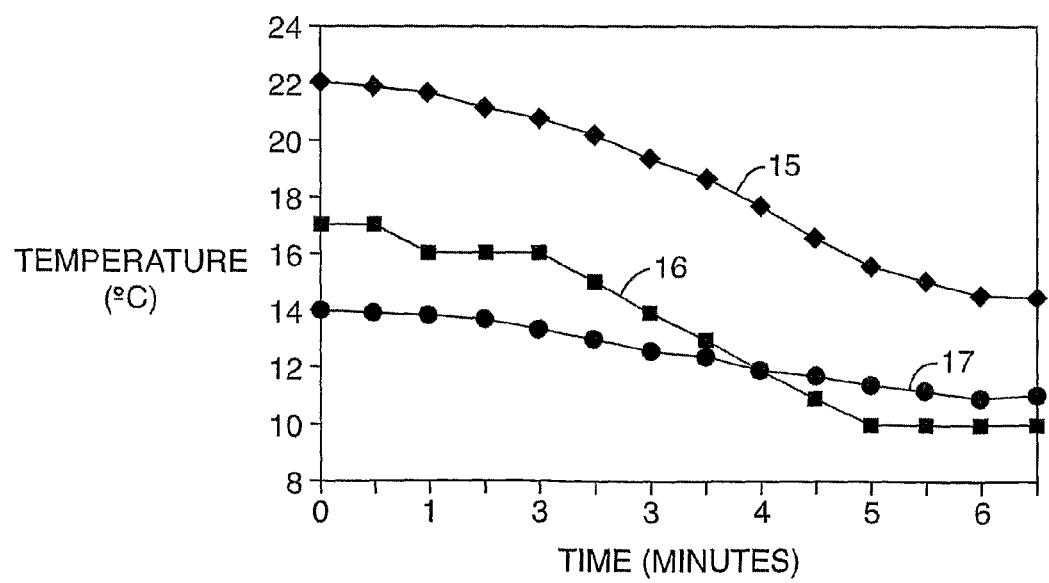
Figure 6:
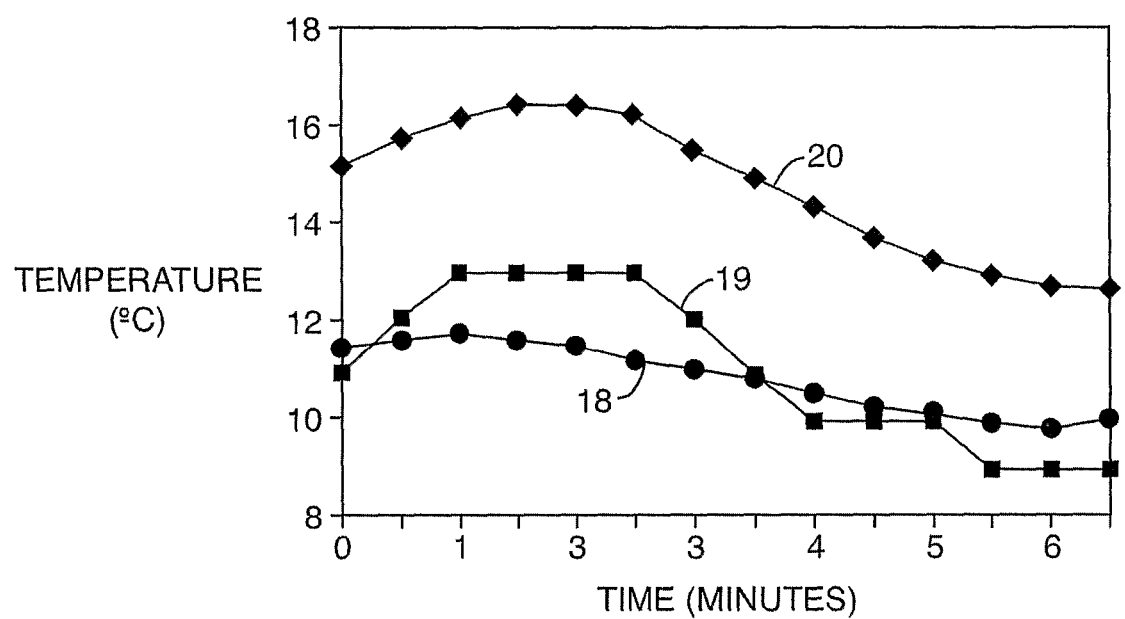
Figure 7A:
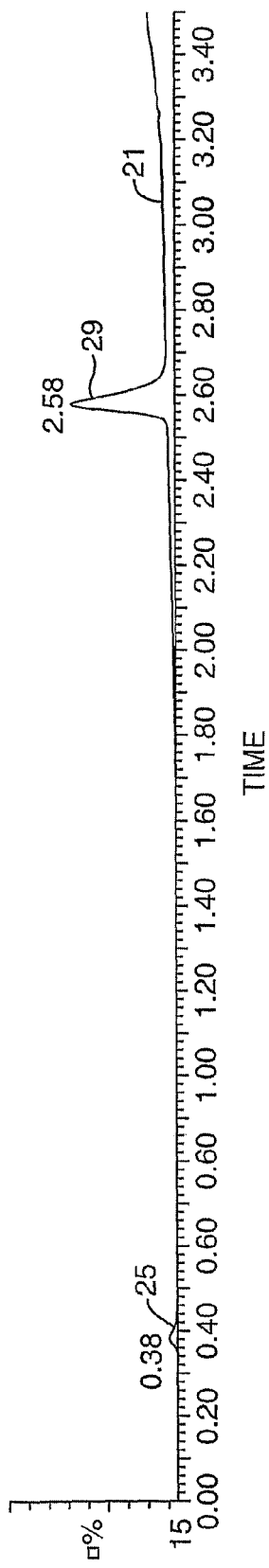
Figure 7B:
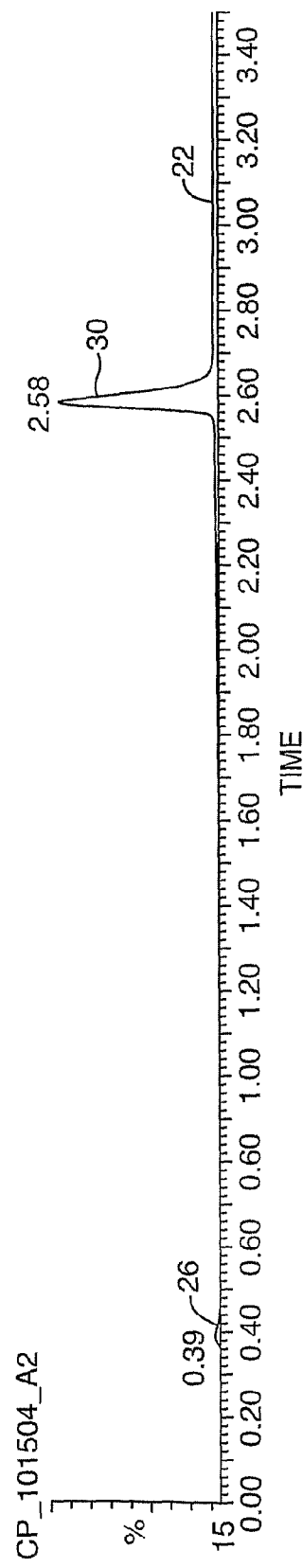
Figure 8A:
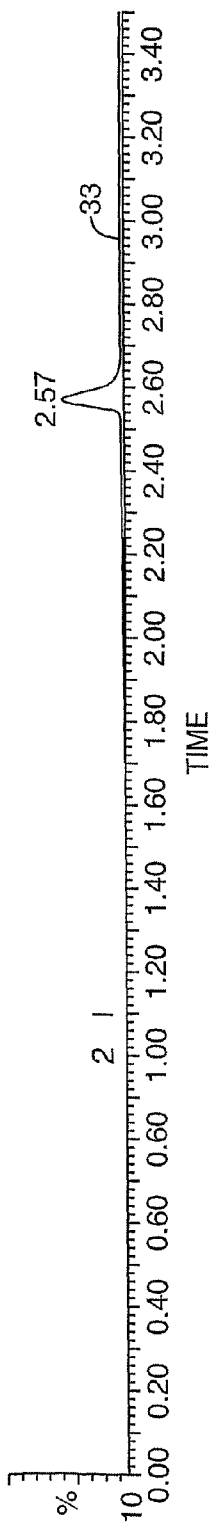
Figure 8B:
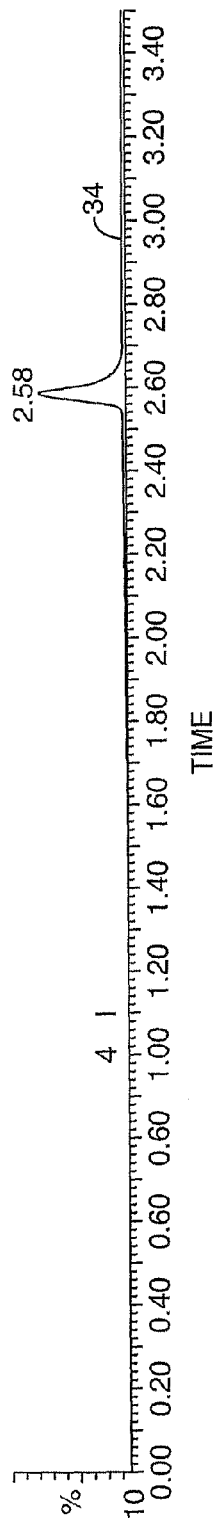
Figure 8C:
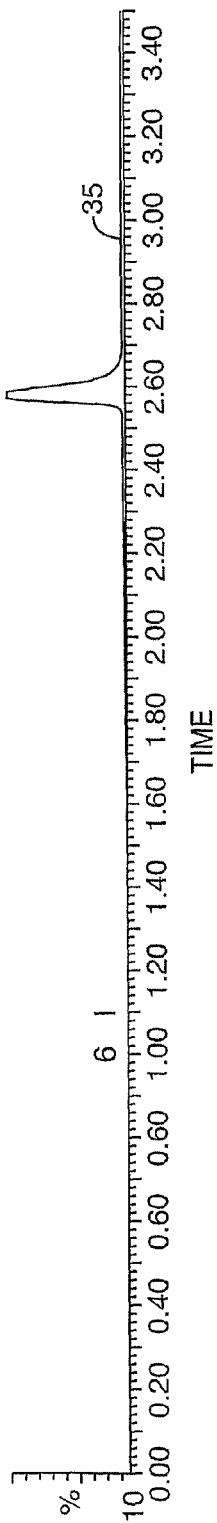
Figure 8D:
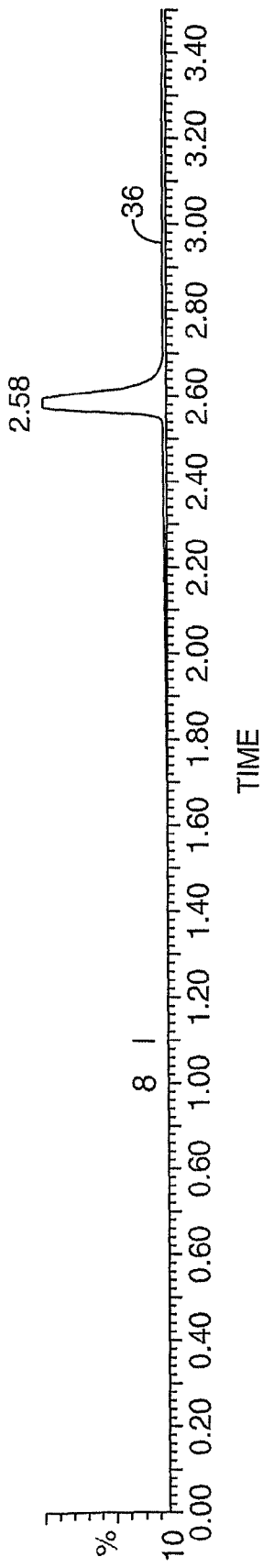
Figure 8E:
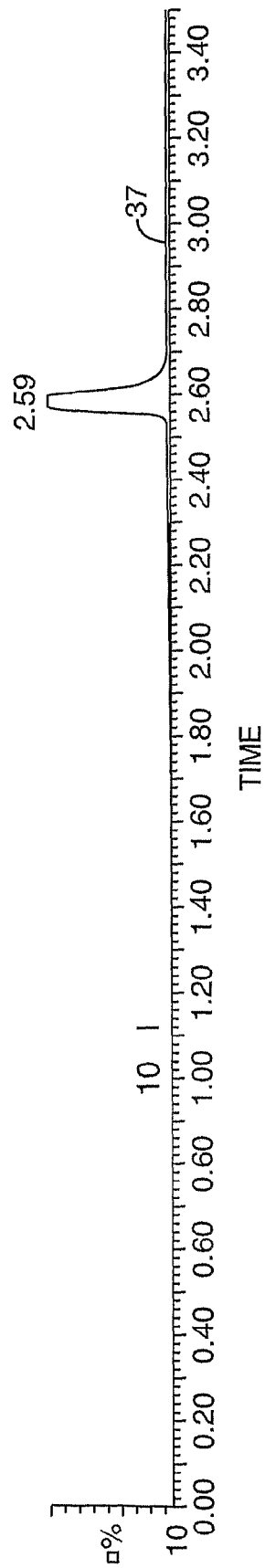

FIGS. 4, 5 and 6 compare the variation in the temperature of the nebulizer chamber with time for two prior ELSD's and an ELSD according to the invention. Referring first to FIG. 4, curves 12, 13 and 14 respectively show the temperature variation observed in the case of prior Waters 2420 detector, a prior Sedex 75 detector (Sedere Inc, 1206, River Road, Cranbury, N.J. 08512-9900, USA) and a Waters 2420 detector fitted with a nebulizer chamber as described above in place of the chamber originally supplied. In each case, the flow of eluent (1.8 ml/minute) was started at time=0 and the temperature of the nebulizer chamber was monitored for a period of three minutes. The drift tube temperature was maintained at 48° C. The composition of the eluent (approximately 90% water, 5% acetonitrile, and 5% of a 1% solution of trifluoroacetic acid in water) remained constant throughout these experiments.

In the case of the modified Waters 2420 detector (curve 14) the chamber was cooled prior to the admission of eluent, as described above. FIG. 4 clearly shows that the temperature of the chamber during the first three minutes of eluent nebulization remains substantially constant using a detector according to the invention (curve 14) but drops significantly in the case of prior detectors (curves 12 and 13).

After the 3-minute period illustrated in FIG. 4 had elapsed, the experiments were continued by starting a gradient elution, during which the composition of the eluent was changed from 90% water, 5% acetonitrile and 5% of the trifluoroacetic acid solution to 0% water, 95% acetonitrile and 5% of the trifluoroacetic acid solution, over a period of 3.5 minutes. This period of gradient elution was followed by a period of 1.5 minutes during which the composition remained constant. The composition of the mobile phase was then very quickly returned to its starting composition (90% water) and held constant for a further 1 minute. The temperature of the nebulizer chamber for each of the three detectors was recorded and is illustrated in FIG. 5, in which curve 15 relates to the prior Waters 2420 detector, curve 16 to the Sedex detector and curve 17 relates to the modified Waters 2420 detector comprising a nebulizer chamber according to the invention. The changing heat load imposed on the nebulization chamber by the nebulization of an eluent of changing composition results in the chamber temperature of all three nebulizers falling, but the temperature variation of the detector according to the invention (curve 17) falls by a smaller amount than it does for either of the two prior detectors (curves 15 and 16).

One minute after the end of the period illustrated in FIG. 5, the gradient elution experiment described for FIG. 5 was repeated. FIG. 6 illustrates the observed temperature changes. The changing heat load due to the varying composition of the eluent again resulted in changes of the nebulizer chamber temperature for all three detectors, but as in the previous experiments the change was smaller in the case of the detector according to the invention (curve 18) than it was for the Sedex detector (curve 19) and the unmodified Waters detector (curve 20). This means that the detector according to the invention, pre-cooled in the absence of a flow of eluent, is ready for use much sooner than the prior detectors, which require a stabilization time of some 15 minutes during which the eluent has to be passed into the detector.

FIGS. 7A-7D further illustrate that a detector as described above is ready for use after a shorter stabilization time than that required for a prior detector. The figures show four chromatograms 21-24 (FIGS. 7A-7D respectively) obtained using a Waters 2420 ELSD fitted with a nebulizer chamber as described above in place of its original chamber. Four consecutive injections of a sample comprising 0.5 mg/ml of flavone dissolved in dimethylsulfoxane (DMSO) were made. The first injection (chromatogram 21) was made three minutes after starting the eluent flow into the ELSD, and the subsequent injections, chromatograms 22-24, were each made immediately after the end of the analysis of the previous injection (approximately 3.5 minutes after its injection). The initial mobile phase composition was 90% water, 5% acetonitrile, 5% of a 1% solution of trifluoroacetic acid in water, and the composition was changed according to the gradient described in respect of FIGS. 5 and 6 above. In FIGS. 7A-7D, peaks 29-32 in chromatograms 21-24 respectively, are the flavone sample. Peaks 25-28 are due to the DMSO solvent. Because DMSO is volatile, it should be lost by evaporation in the nebulizer and drift tube of the ELSD. Any residual DMSO peak is therefore indicative of incomplete desolvation, and if large, an indication that the detector is not ready for use. Chromatograms 21-24 in FIGS. 7A-7D exhibit only very small DMSO peaks, suggesting that desolvation is substantially complete even in the case of the first chromatogram 24. This confirms that the detector is ready for use after only 3 minutes stabilization time.

The stability of a detector as described is further illustrated in FIGS. 8A-8E, which show five chromatograms 33-37 (FIGS. 8A-8E respectively) obtained for 5 different injections of a sample of 0.5 mg/ml of flavone dissolved in DMSO. The volumes injected were 2, 4, 6, 8 and 10 μl for chromatograms 33 to 37 respectively. It can be seen that the DMSO peak is almost undetectable in every case, showing that desolvation remains complete and stable despite the high volumes of injected solvent.

Figure 9A:
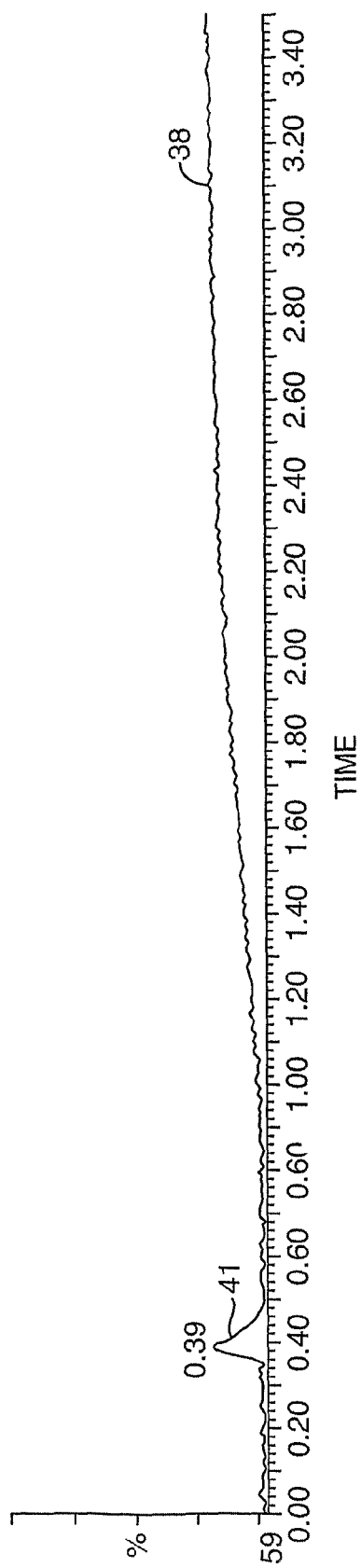
Figure 9B:
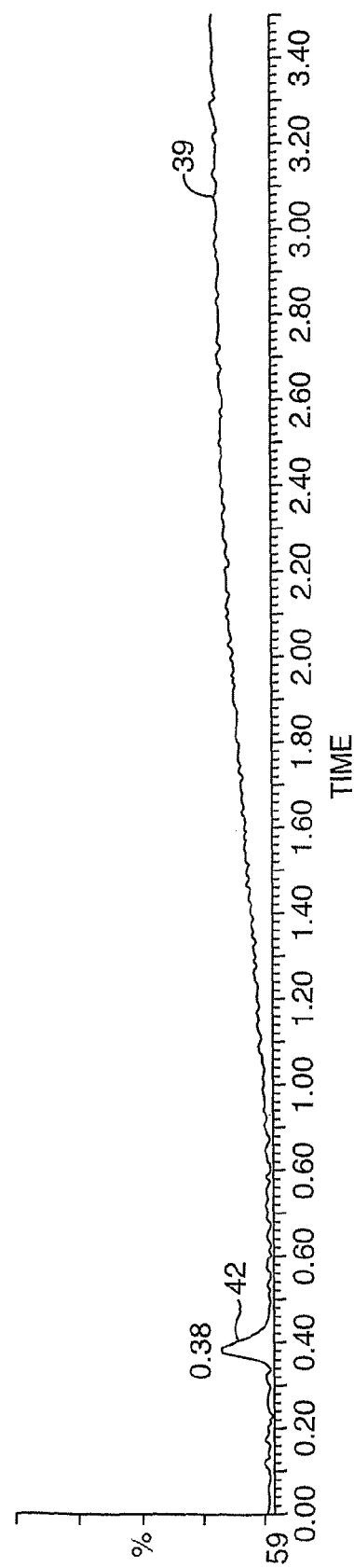

FIGS. 9A-9C show that stable operation and substantially complete desolvation can be obtained for different solvents with a detector having a nebulizer chamber as described above. Chromatogram 38 (FIG. 9A) is the result of an injection of pure DMSO (that is, containing no analyte) recorded with a higher detector sensitivity, but using otherwise identical chromatographic conditions as the experiments shown in FIGS. 7A-7D. Only a small peak 41 due to DMSO peak is visible. Chromatogram 39 (FIG. 9B) is the result of a similar experiment in which the same quantity of isopropyl alcohol was injected, and shows a similar small peak 42. Chromatogram 40 (FIG. 9C) is the result of a similar injection of acetonitrile, and exhibits a small peak 43. In all cases, the small size of the solvent peaks indicates stable operation of the detector with substantially complete desolvation.

What is claimed is:

1. A detector for receiving the eluent from a liquid- or supercritical-fluid chromatograph in which a signal indicative of the presence of an analyte in said eluent is generated by the scattering of light by desolvated particles of said analyte, said detector comprising a nebulizer for generating an aerosol from said eluent in a chamber having a wall that is in good thermal contact with a first heat sink, said first heat sink having a high thermal mass such that the change in temperature of said wall during an analysis of said eluent is minimized, said detector further comprising a heat pump in communication with said first heat sink for removing heat therefrom.

2. A detector as claimed in claim 1 wherein said wall and said first heat sink comprise a single piece of material of high thermal conductivity.

3. A detector as claimed in claim 1 wherein said first heat sink has a high thermal conductivity.

4. A detector as claimed in claim 3 wherein said wall comprises an inert material of low thermal mass in thermal contact with said first heat sink over at least a substantial portion of its surface area.

5. A detector as claimed in claim 4 wherein said wall comprises stainless steel and said first heat sink comprises aluminium.

6. A detector as claimed in claim 1 wherein said heat pump comprises one or more Peltier effect devices which transfer heat from said first heat sink to a second heat sink.

7. A detector as claimed in claim 6 further comprising a fan for cooling said second heat sink.

8. A detector as claimed in claim 1 further comprising a heater for heating said first heat sink.

9. A detector as claimed in claim 1 further comprising a temperature controller that controls the power supplied to said heat pump to control the temperature of said first heat sink.

10. A detector as claimed in claim 9 wherein said heat pump transfers heat from said first heat sink to a second heat sink, said detector further comprising one or both of:

a) a fan for cooling said second heat sink; and
b) a heater for heating said first heat sink;

and wherein said temperature controller controls the power supplied to at least one of said heat pump, said fan or said heater.

11. A detector as claimed in claim 10 which said heat pump comprises one or more Peltier effect devices.

12. A detector for receiving the eluent from a liquid- or supercritical-fluid chromatograph in which a signal indicative of the presence of an analyte in said eluent is generated by the scattering of light by desolvated particles of said analyte, said detector comprising a nebulizer for generating an aerosol from said eluent in a chamber having a wall in good thermal contact with a first heat sink, said detector comprising a heat pump which in use operates to reduce the temperature of said wall below that of its ambient surroundings, at least in the absence of said aerosol.

13. A detector as claimed in claim 12 wherein said heat pump transfers heat from said first heat sink to a second heat sink remote from said wall.

14. A detector as claimed in claim 13 wherein said heat pump comprises one or more Peltier effect devices.

15. A detector as claimed in claim 13 further comprising a fan for cooling said second heat sink.

16. A detector as in claim 12 further comprising a heater for heating said first heat sink.

17. A detector as claimed in claim 13 further comprising a temperature controller for controlling the temperature of said first heat sink and maintaining it below ambient temperature at least in the absence of said aerosol, and one or both of
   a) a fan for cooling said second heat sink; and
   b) a heater for heating said first heat sink;
   wherein said temperature controller controls the power supplied to at least one of said heat pump, said fan or said heater.

18. A detector for receiving the eluent from a liquid- or supercritical-fluid chromatograph in which a signal indicative of the presence of an analyte in said eluent is generated by the scattering of light by desolvated particles of said analyte, said detector comprising a nebulizer for generating an aerosol from said eluent in a chamber having a wall in good thermal contact with a first heat sink, said detector comprising a heat pump which in use operates to reduce the temperature of said wall below that of its ambient surroundings at least in the absence of said aerosol, and said first heat sink having a high thermal mass such that the change in temperature of said wall during the analysis of said eluent is minimized.

19. A detector as claimed in claim 18 wherein said first heat sink has a high thermal conductivity.

20. A detector as claimed in claim 18 wherein said wall comprises an inert material of low thermal mass in thermal contact with said first heat sink over at least a substantial portion of its surface area.

21. A detector as claimed in claim 20 wherein said wall comprises stainless steel and said first heat sink comprises aluminium.

22. A detector as claimed in claim 18 wherein said heat pump comprises one or more Peltier effect devices which transfer heat from said first heat sink to a second heat sink remote from said first heat sink.

23. A detector as claimed in claim 22 further comprising a temperature controller for controlling the temperature of said first heat sink and maintaining it below ambient temperature at least in the absence of said aerosol, and one or both of
   a) a fan for cooling said second heat sink; and
   b) a heater for heating said first heat sink;
   wherein said temperature controller controls the power supplied to at least one of said Peltier effect devices, said fan, or said heater.

24. A detector as claimed in claim 1 further comprising a drift tube having an exit, said drift tube receiving and desolvating droplets of eluent from the nebulizer chamber, a light scattering chamber into which dry particles of analyte may pass from the drift tube, and a manifold surrounding said exit defining an annular space around said exit into which space a sheath gas may be introduced to confine said analyte particles within an annular flow of said sheath gas as they enter said light scattering chamber.

25. A detector as claimed in claim 10 further comprising a drift tube having an exit, said drift tube receiving and desolvating droplets of eluent from the nebulizer chamber, a light scattering chamber into which dry particles of analyte may pass from the drift tube, and a manifold surrounding said exit defining an annular space around said exit into which space a sheath gas may be introduced to confine said analyte particles within an annular flow of said sheath gas as they enter said light scattering chamber.

26. A detector as claimed in claim 18 further comprising a drift tube having an exit, said drift tube receiving and desolvating droplets of eluent from the nebulizer chamber, a light scattering chamber into which dry particles of analyte may pass from the drift tube, and a manifold surrounding said exit defining an annular space around said exit into which space a sheath gas may be introduced to confine said analyte particles within an annular flow of said sheath gas as they enter said light scattering chamber.

27. A method of detecting the presence of an analyte in the eluent from a liquid- or supercritical-fluid chromatograph in which the presence of an analyte in said eluent is indicated by the scattering of light by desolvated particles of said analyte, said method comprising nebulizing said eluent to produce an aerosol in a chamber having a wall, and minimizing the change in temperatures of said wall during an analysis of said eluent by providing a first heat sink in good thermal contact with said wall, said first heat sink having a high thermal conductivity, and pumping heat from said first heat sink to a second heat sink.

28. A method as claimed in claim 27 further comprising pumping said heat through one or more Peltier effect devices.

29. A method as claimed in claim 27 further comprising cooling said second heat sink with a fan.

30. A method as claimed in claim 27 comprising heating said first heat sink with a heater.

31. A method as claimed in claim 28 further comprising providing one or both of
   a) a fan to cool said second heat sink; and
   b) a heater to heat said first heat sink,
and controlling the temperature of said first heat sink by controlling the power supplied to at least one of said Peltier effect devices, said fan, or said heater.

32. A method of detecting the presence of an analyte in the eluent from a liquid- or supercritical-fluid chromatograph in which said presence is indicated by the scattering of light by desolvated particles of said analyte, said method comprising nebulizing said eluent to generate an aerosol in a chamber having a wall, and pumping heat from a first heat sink in thermal contact with said wall to a second heat sink remote from said wall to reduce the temperature of said wall at least prior to the analysis of said eluent and the generation of said aerosol.

33. A method as claimed in claim 32 further comprises pumping said heat through one or more Peltier effect devices.

34. A method as claimed in claim 32 further comprising reducing the temperature of said wall below ambient temperature before the generation of said aerosol is started.

35. A method as claimed in claim 32 further comprising maintaining the temperature of said wall below ambient temperature for at least part of the time during which said aerosol is generated and said eluent is being analysed.

36. A method as claimed in claim 35 wherein said pumping of heat comprises pumping heat through one or more Peltier effect devices and wherein said method further comprises providing one or more of:

a) a fan to cool said second heat sink; and b) a heater to heat said first heat sink;

and controlling the power supplied to at least one of said Peltier effect devices, said fan, and said heater.

\* \* \* \* \*